US00PP21241P2

(12) United States Plant Patent
Ui

(10) Patent No.: US PP21,241 P2
(45) Date of Patent: Aug. 24, 2010

(54) ***CALIBRACHOA* PLANT NAMED 'SAKCAL098'**

(50) Latin Name: ***Calibrachoa* sp.**
Varietal Denomination: SAKCAL098

(75) Inventor: Akinobu Ui, Iwata (JP)

(73) Assignee: Sakata Seed Corporation, Yokohama (JP)

( * ) Notice: Subject to any disclaimer, the term of this patent is extended or adjusted under 35 U.S.C. 154(b) by 0 days.

(21) Appl. No.: 12/378,498

(22) Filed: Feb. 17, 2009

(51) Int. Cl.
*A01H 5/00* (2006.01)

(52) U.S. Cl. ..... Plt./413

(58) Field of Classification Search ..... Plt./413, Plt./356

See application file for complete search history.

*Primary Examiner*—June Hwu
(74) *Attorney, Agent, or Firm*—Jondle & Associates, P.C.

(57) ABSTRACT

'SAKCAL098' is a new *Calibrachoa* cultivar particularly distinguished by having rosy scarlet flower color and a compact growth habit, is disclosed.

1 Drawing Sheet

Genus and species *Calibrachoa* sp.
Variety denomination 'SAKCAL098'.

BACKGROUND OF THE INVENTION

The present invention comprises a new and distinct cultivar of *Calibrachoa,* botanically known as *Calibrachoa* sp., and hereinafter referred to by the cultivar name 'SAKCAL098.' It is characterized by having rosy scarlet flowers and a compact growth habit. 'SAKCAL098' originated from a hybridization made in 2003 in Kakegawa, Japan. The female parent was a proprietary hybrid *Calibrachoa* breeding line named 'K9-326' (unpatented) having a pink flower color and a creeping plant growth habit. The male parent was a proprietary hybrid *Calibrachoa* breeding line named 'K0-213' (unpatented) characterized by its rose flower color and compact plant growth habit.

In November 2003, 'K9-326' and 'K0-213' were crossed and 160 seeds were obtained. In February 2004, the $F_1$ seed was sown in the greenhouse, cultivated and plant lines were produced with flower colors of pink, pink and rosy scarlet with compact plant growth habit. In May 2004, the line 'K5-133' was selected for its rosy scarlet flower color and compact plant growth habit. In July 2004, line K5-133' was vegetatively propagated, cultivated and evaluated. In October 2004, line 'K5-133' was confirmed to be fixed and stable. Line 'K5-133' was propagated again from February to April 2005 to reconfirm the line's stability. The line was subsequently named 'SAKCAL098' and its unique characteristics were found to reproduce true to type in successive generations of asexual propagation via vegetative cuttings.

DESCRIPTION OF THE GENUS *CALIBRACHOA* LLAVE & LEX.

The genus *Petunia* was originally established in 1803 by A. L. Jussieu, who described both *P. parviflora* and *P. nyctaginifloa* as type species. Using a non-horticultural system that selected the first mentioned species as the type species (lectotype), N. L. Britton and H. A. Brown declared *P. parviflora* as the type species for *Petunia* in 1913.

During the 1980's and 1990, H. J. Wijsman published a series of articles regarding the ancestry of *P. hybrida,* the Garden Petunia, and the inter-relationship of several species classified as *Petunia.* These studies discovered that *P. hybrida* and its ancestral species, *P. nyctaginiflora* (=*P. axillaris*) and *P. violacea* (=*P. integrifolia*), possessed 14 pairs of chromosomes while several other species, including *P. parviflora,* possessed 18 pairs of chromosomes. Since *P. parviflora* was the lectotype species for the *Petunia* genus, Wijsman and J. H. de Jong proposed transferring the 14 chromosome species to the genus *Stimoryne.* Horticulturists opposed reclassifying the Garden Petunia and in 1986, Wijsman proposed the alternative of making *P. nyctaginiflora* the lectotype species for *Petunia* and transferring the 18 chromosome species to another genus. The I. N. G. Committee adopted this proposal. By 1990 Wijsman had transferred several species, including *P. parviflora* (=*C. parviflora*) to *Calibrachoa,* originally established by Llave and Lexarza in 1825. *Calibrachoa parviflora* (=*C. mexicana* Llave & Lexarza) is now the type species for the genus *Calibrachoa.*

Classification of the current *Petunia* and *Calibrachoa* species is still in progress. New species are also being identified. Consequently a proper description has not been written for the *Calibrachoa* genus. *Calibrachoa* can, however, be distinguished from *Petunia* based on the higher chromosome number, chromosome morphology, plant branching habit and type of flower bud aestivation. Whereas *Petunia* species bear a flower peduncle and one new stem from a node, *Calibrachoa* bear a flower peduncle and three stems. *Petunia* species have a cochlear corolla bud, and a single outermost petal covers the other four, radially folded and terminally contorted petals. *Calibrachoa* flower buds are flat with all five petals linearly folded and the two lower petals forming a cover around the three other petals and fused together.

SUMMARY OF THE INVENTION

The following are the most outstanding and distinguishing characteristics of this new cultivar when grown under normal horticultural practices in Kakegawa, Japan.

1. Rosy scarlet flower color; and
2. Compact growth habit.

DESCRIPTION OF PHOTOGRAPHS

This new *Calibrachoa* plant is illustrated by the accompanying photographs which show the plant's form, foliage and flowers. The colors shown are as true as can be reasonably obtained by conventional photographic procedures.

DESCRIPTION OF THE NEW CULTIVAR

Figure 1:
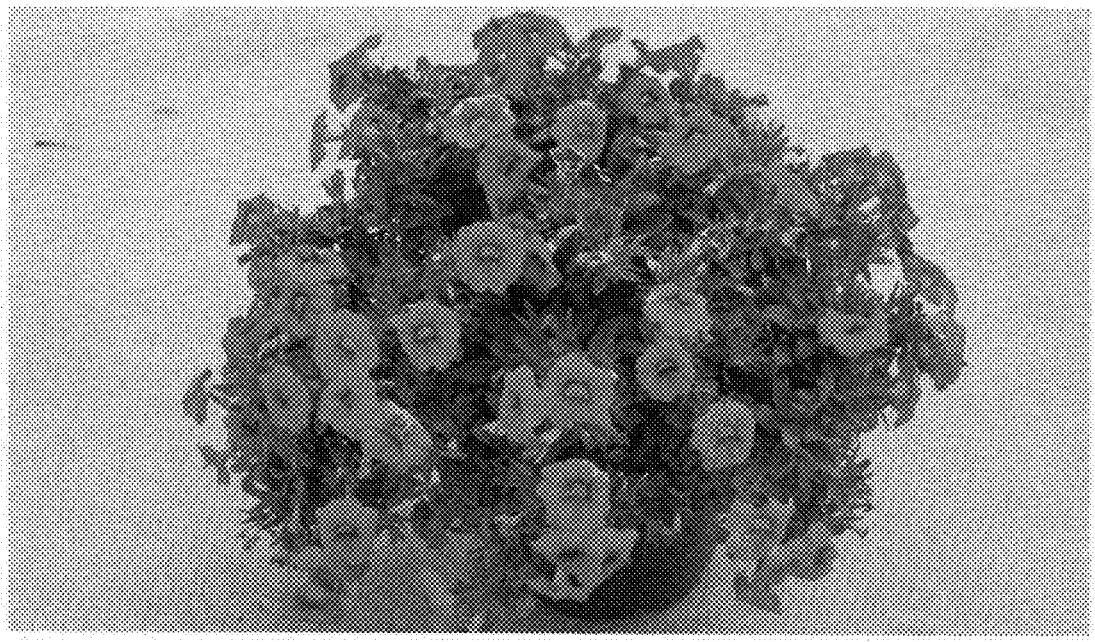
FIG. 1 shows overall plant habit.
Figure 2:
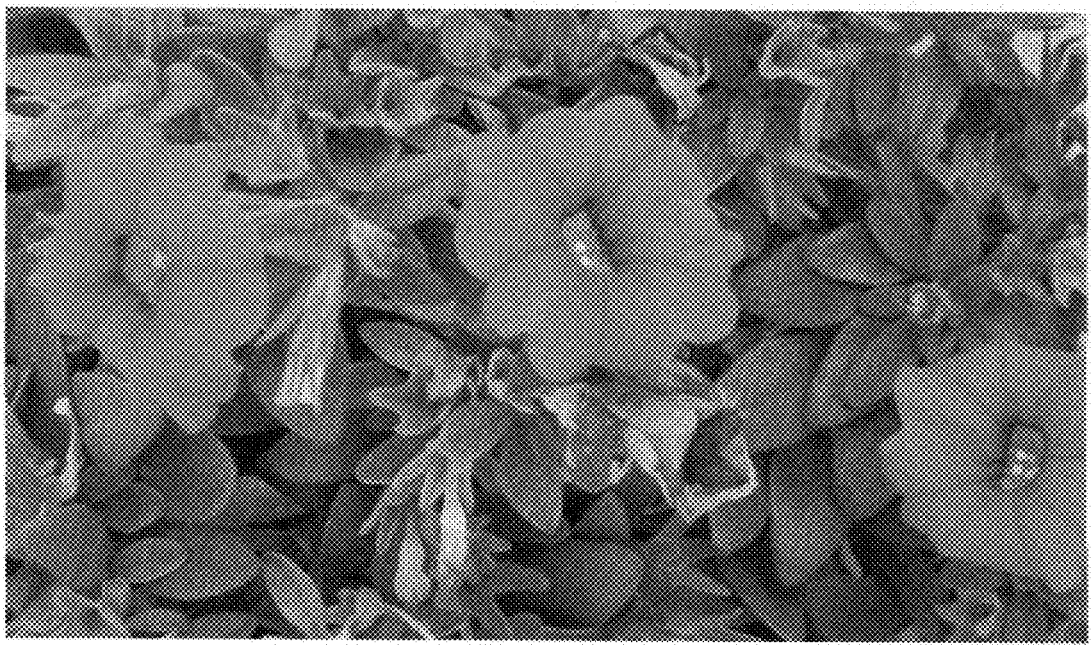
FIG. 2 shows foliage and mature flowers.

The following detailed description sets forth the distinctive characteristics of 'SAKCAL098'. The data which define these characteristics were collected from asexual reproductions carried out in Salinas, Calif. The detailed description was taken from plants grown under greenhouse conditions for approximately 7 months from stick date. Color references are to The RHS Colour Chart of The Royal Horticultural Society of London (RHS), $4^{th}$ Edition.

DETAILED BOTANICAL DESCRIPTION

Classification:
- *Family.*—Solanaceae.
- *Botanical.*—*Calibrachoa* sp. cultivar 'SAKCAL098'.
- *Common name.*—*Calibrachoa.*

Parentage:
- *Female.*—Hybrid proprietary *Calibrachoa* breeding line 'K9-326' (unpatented).
- *Male.*—Hybrid proprietary *Calibrachoa* breeding line 'K0-213' (unpatented).

Plant description:
- *Life cycle.*—Tender perennial.
- *Form.*—Branching.
- *Habit.*—Compact.
- *Height* (*from soil line to top of foliage*).—15.0 cm.
- *Spread.*—35.0 cm.

Propagation:
- *Type cuttings.*—Vegetative cuttings.
- *Time to produce a rooted cutting.*—6 weeks.
- *Time to bloom from propagation.*—10 weeks.

Environmental conditions for plant growth: The terminal 1.0 to 1.5 inches of an actively growing stem was excised. The vegetative cuttings were propagated in five to six weeks. The base of the cuttings were dipped for 1 to 2 seconds in a 1:9 solution of DIP 'N GROW (1 solution: 9 water) root inducing solution immediately prior to sticking into the cell trays. Cuttings were stuck into plastic cell trays having 98 cells, and containing a moistened peat moss-based growing medium. The cuttings were misted with water from overhead for 10 seconds every 30 minutes until sufficient roots were formed. Rooted cuttings were transplanted and grown in 12 cm diameter plastic pots in a glass greenhouse located in Salinas, Calif. Pots contained a peat moss-based growing medium. Soluble fertilizer containing 20% nitrogen, 10% phosphorus and 20% potassium was applied once a day or every other day by overhead irrigation. Pots were top-dressed with a dry, slow release fertilizer containing 20% nitrogen, 10% phosphorus and 18% potassium. The typical average air temperature was 24° C.

Stems:
- *Stem color.*—RHS 144B (Yellow-green).
- *Anthocyanin color.*—Absent.
- *Pubescence.*—Slight.
- *Pubescence color.*—RHS N155A (White).
- *Stem description.*—Dull texture; circular cross-section.
- *Stem diameter.*—0.2 cm.
- *Stem length.*—10.0 cm.
- *Internode length.*—1.0 cm (Average).

Leaves:
- *Arrangement.*—Alternate.
- *Shape.*—Elliptic.
- *Apex.*—Obtuse.
- *Base.*—Attenuate.
- *Attachment.*—Decurrent (no petiole).
- *Margin.*—Entire.
- *Surface* (*both upper and lower*).—Dull.
- *Surface pubescence* (*both upper and lower*).—Slight.
- *Pubescence color.*—RHS N155A (White).
- *Venation.*—Pinnate.
- *Length.*—3.5 cm.
- *Width.*—1.4 cm.
- *Color* (*both surfaces*).—RHS 147B (Yellow-green).
- *Fragrance.*—Absent.

Flowers:
- *Flowering habit.*—Indeterminate.
- *Flower type.*—Solitary.
- *Flowering requirements.*—Will flower so long as day length is greater than 12 hours and temperature exceeds 13° C.
- *Duration of flowers.*—About 5 days.
- *Blooming season.*—April to September.
- *Corolla.*—5 petals, fused.
- *Corolla shape.*—The flowers are funnel shaped with five fissures and a shallow, yet prominent, indentation of the petal tip at the midvein.
- *Fragrance.*—Absent.

Flower buds:
- *Surface.*—Pubescent.
- *Length.*—2.2 cm.
- *Diameter.*—0.5 cm.
- *Shape.*—Ovate.
- *Color.*—RHS 61A (Red-purple).
- *Peduncle.*—Length: 0.7 cm. Diameter: 0.1 cm. Color: RHS 144C (Yellow-green). Texture: Moderate pubescence. Appearance: Dull. Pubescence color: RHS N155A (White).

Flower description:
- *Flower diameter.*—3.0 cm.
- *Flower depth.*—2.0 cm.
- *Flower tube length.*—1.5 cm.
- *Flower tube diameter.*—0.8 cm.
- *Calyx.*—5 sepals, free.
- *Sepals.*—Shape: Elliptical. Apex: Obtuse. Margin: Entire. Sepal color (both surfaces): RHS 143C (Green).
- *Petals.*—Shape: Bilabiate, fused; shallow, yet prominent indentation of the petal tip at the mid-vein. Length: 1.0 cm. Width: 1.3 cm. Apex: Truncate. Margin: Entire. Texture: Glabrous. Color: Lobe color: Upper lobe: RHS 50A (Red). Lower lobe: RHS 63B (Red-purple). Corolla tube color: Inner: RHS 13A (Yellow) with RHS 187A. (Greyed-purple) veins. Outer: RHS 13C (Yellow) with RHS 187A. (Greyed-purple) veins.
- *Fragrance.*—Absent.

Reproductive organs:
- *Stamen number.*—5, free.
- *Stamen color.*—RHS 154C (Yellow-green).
- *Pollen color.*—RHS 13C (Yellow).
- *Ovary.*—Superior.
- *Placenta arrangement.*—Central.
- *Pistil number.*—1 (per inflorescence).
- *Pistil length.*—0.7 cm.
- *Stigma color.*—RHS 144B (Yellow-green).
- *Style length.*—0.6 cm.
- *Style color.*—RHS 144C (Yellow-green).

Fruit/seed set: No fruit or seeds produced at all.

Disease and Insect Resistance: Excellent resistance to rain, heat and drought. Will not tolerate temperature below 10° C. Plants are susceptible to *Botrytis*, powdery mildew, various stem and root rots, and certain viruses, like Tobacco Mosaic Virus and Impatiens Necrotic Spotted Virus. Plants can be infested with aphids, leafminer, whitefly and various *Lepidoptera*.

COMPARISON WITH PARENTAL LINES AND KNOWN CULTIVARS

'SAKCAL098' is distinguished from its parents mainly by flower color and plant growth habit as shown in Table 1 below.

TABLE 1

| Characteristic | 'SAKCAL098' | Female Parent: 'K9-326' | Male Parent: 'K0-213' |
|---|---|---|---|
| Flower color | Red | Pink | Rose |
| Plant growth habit | Compact | Creeping | Compact |

*Calibrachoa* 'SAKCAL098' is a distinct variety of *Calibrachoa* due to its rosy scarlet flower color and compact plant growth habit. 'SAKCAL098' is most similar to the variety 'Uscali28' (U.S. Plant Pat. No. 14,847). However, there are differences in the flower petal color, flower size and plant growth habit as described in the table below (color references are to The Royal Horticultural Society Colour Chart, 4$^{th}$ edition):

TABLE 2

| Characteristic | 'SAKCAL098' | 'Uscali28' |
|---|---|---|
| Flower petal color, upper surface | RHS 50A (Red) | RHS 53A (Red) |
| Flower petal color, lower surface | RHS 63B (Red-purple) | RHS 186A (Greyed-purple) |
| Flower size (diameter) | 3.0 cm | 2.9 cm |
| Plant growth habit | Compact | Semi-upright |

We claim:

1. A new and distinct cultivar of *Calibrachoa* plant as shown and described herein.

* * * * *